US012190236B2

(12) United States Patent
Obika et al.

(10) Patent No.: US 12,190,236 B2
(45) Date of Patent: Jan. 7, 2025

(54) PREDICTING PROPERTIES OF MATERIALS FROM PHYSICAL MATERIAL STRUCTURES

(71) Applicant: DeepMind Technologies Limited, London (GB)

(72) Inventors: Annette Ada Nkechinyere Obika, London (GB); Tian Xie, Cambridge, MA (US); Victor Constant Bapst, London (GB); Alexander Lloyd Gaunt, Ely (GB); James Kirkpatrick, London (GB)

(73) Assignee: DeepMind Technologies Limited, London (GB)

( * ) Notice: Subject to any disclaimer, the term of this patent is extended or adjusted under 35 U.S.C. 154(b) by 879 days.

(21) Appl. No.: 17/240,554

(22) Filed: Apr. 26, 2021

(65) Prior Publication Data

US 2021/0334655 A1    Oct. 28, 2021

Related U.S. Application Data

(60) Provisional application No. 63/015,328, filed on Apr. 24, 2020.

(51) Int. Cl.
*G06N 3/08*  (2023.01)
*G06N 3/04*  (2023.01)

(52) U.S. Cl.
CPC .............. *G06N 3/08* (2013.01); *G06N 3/04* (2013.01)

(58) Field of Classification Search
CPC .. G06N 3/08; G06N 3/04; G06N 3/06; G06N 3/063
See application file for complete search history.

(56) References Cited

U.S. PATENT DOCUMENTS

| | | | | |
|---|---|---|---|---|
| 10,830,747 | B2* | 11/2020 | Agrawal | G06F 30/20 |
| 11,587,646 | B2* | 2/2023 | Colby | G06N 3/042 |
| 11,901,045 | B2* | 2/2024 | Katsuki | G06N 5/04 |
| 2022/0044769 | A1* | 2/2022 | Ramprasad | G06N 3/048 |

OTHER PUBLICATIONS

Bartel et al., "A critical examination of compound stability predictions from machine learned formation energies," npj Computational Materials, 6(97): 11 pages.

(Continued)

*Primary Examiner* — Kamran Afshar
*Assistant Examiner* — Brian J Hales
(74) *Attorney, Agent, or Firm* — Fish & Richardson P.C.

(57) ABSTRACT

Methods, computer systems, and apparatus, including computer programs encoded on computer storage media, for predicting one or more properties of a material. One of the methods includes maintaining data specifying a set of known materials each having a respective known physical structure; receiving data specifying a new material; identifying a plurality of known materials in the set of known materials that are similar to the new material; determining a predicted embedding of the new material from at least respective embeddings corresponding to each of the similar known materials; and processing the predicted embedding of the new material using an experimental prediction neural network to predict one or more properties of the new material.

18 Claims, 5 Drawing Sheets

(56) References Cited

OTHER PUBLICATIONS

Battaglia et al., "Relational inductive biases, deep learning, and graph networks," CoRR, Jun. 2018, arxiv.org/abs/1806.01261, 40 pages.
Butler et al., "Machine learning for molecular and materials science," Nature, Jul. 2018, 559:547-555.
Carleo et al., "Machine learning and the physical sciences," Rev. Mod. Phys., Dec. 2019, 91:045002.
Chen et al., "Graph networks as a universal machine learning framework for molecules and crystals," Chem. Mater., Apr. 2019, 31(9):3564-3572.
Cohen et al., "Challenges for density functional theory," Chemical Reviews, Dec. 2011, 112(1):289-320.
Cohen et al., "Insights into current limitations of density functional theory," Science, Aug. 2008, 321(5890):792-794.
Curtarolo et al., "AFLOW: An automatic framework for high-throughput materials discovery," Computational Materials Science, Jun. 2012, 58:218-226.
Dunn et al., "Benchmarking materials property prediction methods: the matbench test set and automatminer reference algorithm," npj Computational Materials, Sep. 2020, 6(138):1-10.
Duvenaud et al., "Convolutional networks on graphs for learning molecular fingerprints," CoRR, Sep. 2015, arxiv.org/abs/1509.09292, 9 pages.
Faber et al., "Prediction errors of molecular machine learning models lower than hybrid DFT error," J. Chem. Theory Comput., Sep. 2017, 13(11):5255-5264.
Ghiringhelli et al., "Big data of materials science: critical role of the descriptor," Phys. Rev. Lett., Mar. 2015, 114:105503.
Hellenbrandt et al., "The inorganic crystal structure database (icsd)—present and future," Crystallography Reviews, 2004, 10(1):17-22.
Isayev et al., "Universal fragment descriptors for predicting properties of inorganic crystals," Nature Communications, Jun. 2017, 8(15679):1-12.
Jain et al., "Commentary: The materials project: A materials genome approach to accelerating materials innovation," APL Materials, 1:011002.
Jain et al., "Formation enthalpies by mixing gga and gga+ u calculations," Physical Review B, Jul. 2011, 84:045115.
Jha et al., "Deep learning the chemistry of materials from only elemental composition," Scientific Reports, 8(17593):13 pages.
Jha et al., "Enhancing materials property prediction by leveraging computational and experimental data using deep transfer learning," Nature Communications, Nov. 2019, 10(5316): 12 pages.
Kim et al., "Experimental formation enthalpies for intermetallic phases and other inorganic compounds," Scientific Data, Oct. 2017, 4(170162):11 pages.
Kirklin et al., "The open quantum materials database (oqmd): assessing the accuracy of dft formation energies," npj Computational Materials, Dec. 2015, 1(15010):15 pages.
Lany, "Semiconductor thermochemistry in density functional calculations," Physical Review B, 78:245207.
Ong et al., "Python materials genomics (pymatgen): A robust, open-source python library for materials analysis," Computational Materials Science, Feb. 2013, 68:314-319.
Ouyang et al., "Sisso: A compressed-sensing method for identifying the best low-dimensional descriptor in an immensity of offered candidates." Physical Review Materials, Aug. 2018, 2:083802.
Saal et al., "Materials design and discovery with high-throughput density functional theory: The open quantum materials database (oqmd)," JOM, Sep. 2013, 65:1501-1509.
Scarselli et al., "The graph neural network model," IEEE Transactions on Neural Networks, Jan. 2009, 20(1):61-80.
Schmidt et al., "Recent advances and applications of machine learning in solid-state materials science," npj Computational Materials, Aug. 2019, 5(83):36 pages.
Schutt et al., "Schnet—a deep learning architecture for molecules and materials," The Journal of Chemical Physics, Mar. 2018, 148:241722.
Senior et al., "Improved protein structure prediction using potentials from deep learning," Nature, Jan. 2020, 577:706-710.
Silver et al., "A general reinforcement learning algorithm that masters chess, shogi, and Go through self-play," Science, Dec. 2018, 362(6419):1140-1144.
Szegedy et al., "Inception-v4, inception-resnet and the impact of residual connections on learning," Thirty-First AAAI Conference on Artificial Intelligence, Feb. 2017, 31(1):4278-4284.
Van Den Oord et al., "Pixel recurrent neural networks," Proceedings of the 33rd International Conference on Machine Learning, 2016, 48:1747-1756.
Vaswani et al., "Attention is all you need," CoRR, Jun. 2017, arxiv.org/abs/1706.03762, 15 pages.
Xie et al., "Crystal graph convolutional neural networks for an accurate and interpretable prediction of material properties," Phys. Rev. Lett., Apr. 2018, 120(145301):15 pages.
Yang et al., "Analyzing learned molecular representations for property prediction," J. Chem. Inf. Model, Jul. 2019, 59(8):3370-3388.
Zaheer et al., "Deep sets," CoRR, Mar. 2017, arxiv.org/abs/1703.06114, 29 pages.
Zhang et al., "A strategy to apply machine learning to small datasets in materials science," npj Computational Materials, May 2018, 4(25):1-8.

\* cited by examiner

PREDICTING PROPERTIES OF MATERIALS FROM PHYSICAL MATERIAL STRUCTURES

CROSS-REFERENCE TO RELATED APPLICATION

This application claims priority under 35 U.S.C. 119 to Provisional Application No. 63/015,328, filed Apr. 24, 2020, which is incorporated by reference.

BACKGROUND

This specification relates to using neural networks to predict properties of physical materials.

Neural networks are machine learning models that employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters.

SUMMARY

This specification describes a system implemented as computer programs on one or more computers in one or more locations that predicts one or more properties of a physical material, e.g., as part of a materials discovery pipeline. Predicting the properties of the physical material using a neural network can accelerate materials discovery, i.e., because physical experiments on the material do not need to be performed to ascertain the values of the one or more properties, or provide new information about existing physical materials.

The description below describes the one or more properties that are being predicted as including an energy of formation of a solid material. However, in practice, the one or more properties can include one or more other properties instead of or in addition to the energy of formation. Examples of other properties include electronic properties such as band gap or resistivity of the material.

To predict one or more properties of a new material, the system maintains data specifying a set of known materials each having a respective known physical structure, e.g., an atomistic structure of the material. For example, the set of known materials may be materials represented in a dataset of material simulations, i.e., materials whose physical structure has been determined through simulation and for which values of the one or more properties have been simulated through the simulation.

The system receives data specifying the new material, e.g., a chemical formula for the new material.

The system then identifies a plurality of known materials in the set of known materials that are similar to the new material. For example, the system can use a technique, e.g., a phase diagram decomposition, that generates a representation of the new material as a weighted combination of a subset of the known materials in the set and that assigns a respective weight to each of the plurality of known materials in the subset.

The system then determines a predicted embedding of the new material from at least respective embeddings corresponding to each of the similar known materials. Each respective embedding represents the respective known physical structure of the corresponding similar known material, e.g., the atomistic structure of the similar known material that was determined through simulation.

The system then processes the predicted embedding of the new material using an experimental prediction neural network to predict one or more properties of the new material.

Thus, the system generates the prediction of the one or more properties of the new material by leveraging features of the physical structure of the known physical materials, even though the system did not have access to the physical structure of the new material.

The described techniques predict one or more properties of a physical material using a neural network. Predicting the properties of the physical material using a neural network can accelerate materials discovery, i.e., because physical experiments on the material do not need to be performed to ascertain the values of the one or more properties.

A key difficulty when applying machine learning in Materials Science is that experimental datasets of material properties tend to be small. By applying the described techniques, material descriptors can be learned from the structures present in large scale datasets of material simulations and these descriptors can be used to improve the prediction of experimental properties. Using learned features, i.e., embeddings generated using a graph neural network and based on the structure of materials, for experimental property predictions outperforms existing methods that are based solely on chemical composition. Moreover, the described techniques can be effectively used to generalize to new materials, improving the performance of the system when generalization requirements of the task are made more stringent, for example when limiting the amount of training data or when generalizing to unseen chemical spaces.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

A difficulty when applying machine learning in materials science is that experimental datasets of material properties tend to be limited. High quality experimental data requires expensive laboratory measurements. Thus, available experimental datasets usually only cover limited material diversity.

An alternative source of data is simulation data for material properties. For example, quantum mechanical simulations, e.g. density functional theory (DFT) simulations, have been used to create datasets of material properties covering a significantly larger material space. The simulation data may not have adequate accuracy for predicting material properties. For example, DFT methods tend to produce large systematic errors due to the limitations of the underlying density functional approximations as well as other effects like the OK approximation.

In order to address the above challenges, the described techniques leverage the information in large simulation databases by learning a transferable embedding that enables accurate experimental property prediction even from small amounts of experimental data. By applying the described techniques, material descriptors can be learned from the structures present in large scale datasets of material simulations and these descriptors can be used to improve the prediction of experimental properties. Using learned features, i.e., embeddings generated using a graph neural network and based on the structure of materials, for experimental property predictions outperforms existing methods that are based solely on chemical composition. Moreover, the described techniques can be effectively used to generalize to new materials, improving the performance of the system when generalization requirements of the task are made more stringent, for example when the amount of training data is limited or when generalizing to unseen chemical spaces.

Figure 1:
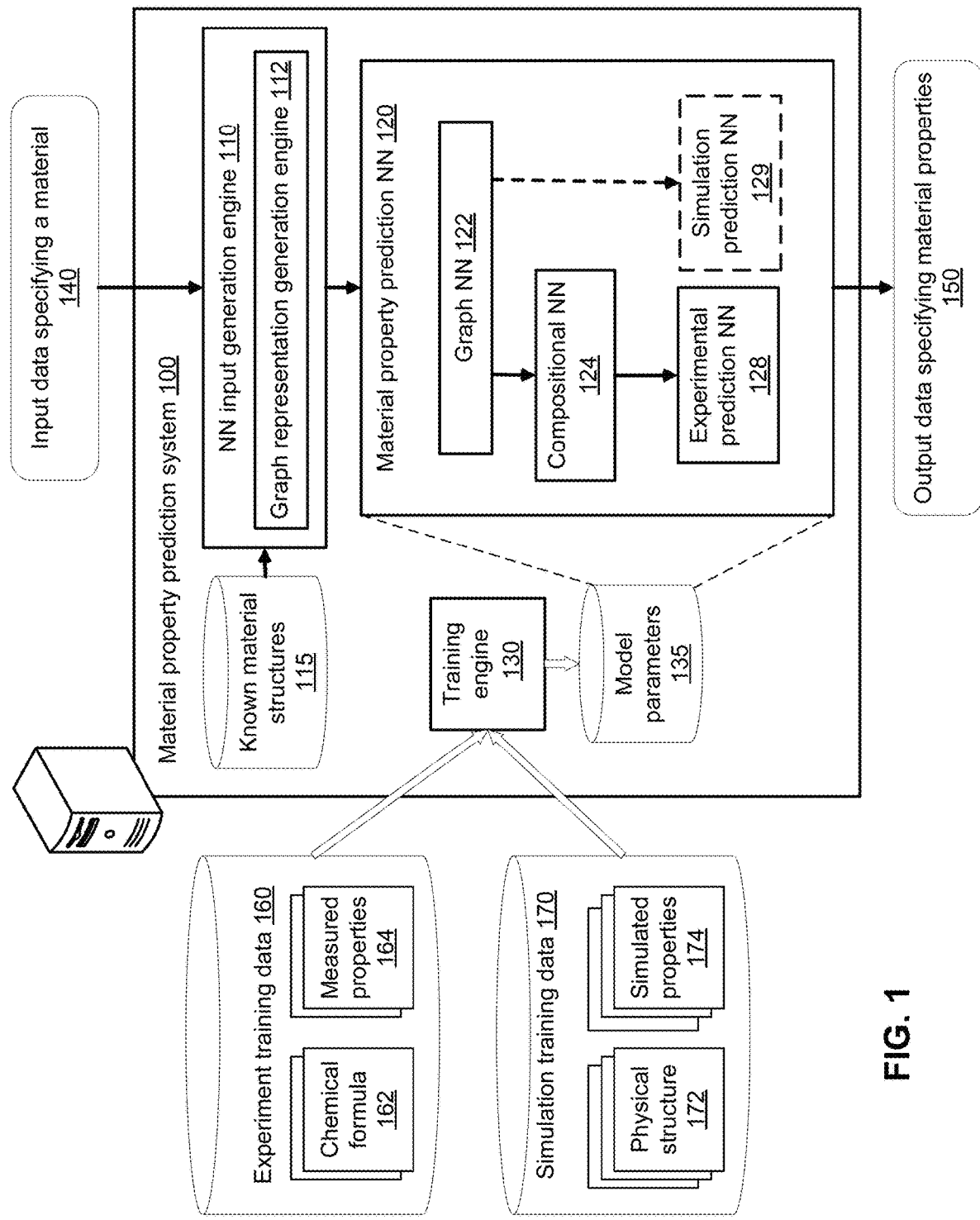
FIG. 1 shows an example of a material property prediction system.

FIG. 1 shows an example of a material property prediction system 100. The system 100 is an example of a system implemented as computer programs on one or more computers in one or more locations, in which the systems, components, and techniques described below can be implemented.

In general, the material property prediction system 100 predicts one or more properties of a new material using a material property prediction neural network and based on physical structures of one or more known materials that are similar to the new material. The parameters of the material property prediction neural network are obtained by training the neural network on experimental training data and simulation training data.

As shown in FIG. 1, the material property prediction system 100 maintains data 115 specifying a set of known materials each having a respective known physical structure, e.g., an atomistic structure of the material. The system receives input data 140 specifying the new material, e.g., a chemical formula for the new material, and generates output data 150 specifying one or more predicted properties of the new material using neural network processing.

The material property prediction system 100 includes a neural network input generation engine 110 that generates a neural network input based on the input data 140 and the dataset 115 of the known material structures for the neural network processing. The neural network input generation engine 110 includes a graph representation generation engine 112 for obtaining one or more graph representations of material physical structures of one or more known materials specified in the dataset 155 that are similar to the new material. An example of graph representation 214 of a material physical structure 212 is illustrated in portion (A) of FIG. 2.

The neural network input can include the one or more graph representations. In some implementations, the neural network input can further include one or more material properties of one or more known materials specified in the dataset 115.

The system 100 processes the neural network input using the material property prediction neural network 120 to generate the output data 150.

The material property prediction neural network 120 includes a graph neural network 122 that processes a graph representation of a material physical structure to generate an embedding corresponding to the material physical structure and an experimental prediction neural network 128 that processes an experimental embedding of a material to predict one or more properties of the material.

Each of the graph neural network 122, the compositional neural network 124, the experimental prediction neural network 128, and the simulation prediction neural network 129, can be implemented with any suitable network architecture, and can include one or more fully-connected layers, convolution layers, rectified linear unit layers, batch normalization layers, or pooling layers. The graph neural network can further include one or more message passing layers that operate on the feature representations of the nodes and edges of the graph representation of the material structure. The experimental prediction neural network 128 and the simulation prediction neural network 129 can be feedforward neural networks each configured to regress an input embedding to predicted values of the one or more material properties. An example of the feedforward neural network is a multi-layer perceptron (MLP) network.

In some implementations, the material property prediction neural network 120 further includes a compositional neural network 124 that processes an embedding outputted by the graph neural network 122 to generate an experimental embedding. The experimental embedding can be used as the input of the experimental prediction neural network 128.

Examples of generating the neural network input and processing the neural network input using the material property prediction neural network 120 to generate the output data 150 will be described below with references to FIG. 2, FIG. 3A, and FIG. 3B.

Briefly, the neural network input generation engine 110 determines whether the new material specified in the input data 140 has a stable correspondence to (e.g., has the same chemical composition as) any of the known materials in the dataset 115. If the neural network input generation engine 110 determines that the new material does not have a stable correspondence to any of the known materials in the set, the neural network input generation engine 110 generates a representation of the new material x as a weighted combination of the plurality of similar known materials using a process such as phase diagram decomposition.

After identifying the weighted combination of the plurality of similar known materials, the graph representation generation engine 112 generates a graph representation of each similar known material based on the physical structure (e.g. atomistic structure) of the similar known material. The system 100 processes the graph representation with the graph neural network 122 to generate an embedding of the similar known material.

In some implementations, the physical structure and other properties of a similar known material were determined through simulations that model the atomistic structures of the material, such as using the DFT calculations. For such a similar known material, the embedding is an embedding based on simulated material features. The system 100 can process an input that includes the embedding with the compositional neural network 124 to generate an experimental embedding of the similar known material.

Once the respective experimental embeddings for the plurality of similar known materials are obtained, the system 100 determines a predicted embedding of the new material by performing interpolation of the experimental embeddings of the similar known materials according to the weight coefficients of the weighted combination of the plurality of similar known materials. Then, the system 100 processes the predicted embedding of the new material using the experimental prediction neural network 128 to predict one or more properties of the new material.

If neural network input generation engine 110 the system determines that the new material does have a stable correspondence to a known material, the system 100 generates the embedding of the known material based on the embedding of the known material, and proceeds to predict the one or more properties of the new material based on the embedding of the known material using the compositional neural network 124 and the experimental prediction neural network 128.

Examples of the predicted properties of the new material specified by the output data include the formation energy, the energy of decomposition, the band gap, and/or the resistivity of the new material. Predictions of these properties have various applications in material characterization and discovery. For example, the formation energy and the energy of decomposition can be used to predict whether a given material (e.g. an alloy) is stable, and if not, which compounds the material will potentially decompose into. The resistivity and band gap are crucial for predicting the electronic properties of a functional material and thus have applications across all of electronics.

In some implementations, the material property prediction neural network 120 further includes a simulation prediction neural network 129 to facilitate a training process using simulation data. The simulation prediction neural network processes the embedding outputted by the graph neural network to predict the one or more material properties of a material corresponding to the embedding.

The system 100 can further include a training engine 130 that performs training of the material property prediction neural network 120. The training engine 130 updates the model parameters 135 of the material property prediction neural network 120, including, e.g., weight and bias parameters of the graph neural network, compositional neural network 124, experimental prediction neural network 128, and simulation prediction neural network 129 based on experimental training data 160 and simulation training data 170.

The experimental training data 160 includes experimental training examples each specifying one of a plurality of materials for which experimental measurements have been performed to obtain one or more material properties. Each experimental training example includes experimentally measured values for each of the one or more properties of the corresponding material as data labels 164. For example, each experimental training example can include one or more experimentally measured values for the formation energy, the energy of decomposition, the band gap, and/or the resistivity of the corresponding material.

In some implementations, each experimental training example includes a chemical composition (e.g., a chemical formula 162) of the corresponding material to specify the material.

The simulation training data 170 includes a plurality of simulation training examples that respectively specify a plurality of materials for which simulations have been performed to predict one or more material properties. Each simulation training example includes a physical structure 172 and simulated values for each of the one or more properties as the data label 174 of the corresponding material.

The physical structure 172 can be an atomistic structure, for example, an atomistic structure of a unit cell of the crystal, which specifies the coordinates of each atom in the unit cell of the crystal, of the corresponding material.

In some implementations, the physical structure of the material was determined through simulations that model the atomistic structures of the material, such as using the density functional theory (DFT) simulations.

The simulated values of the material's properties can also be obtained in a simulation of the material. For example, the simulation training example can include one or more simulated values for the formation energy, the energy of decomposition, the band gap, and/or the resistivity of the corresponding material computed through simulations that model the atomistic structures of the material, such as using the DFT simulations.

In some implementations, since simulation data is relatively inexpensive to obtain, the simulation training data 170 can include a relatively large number of simulation training examples compared to the experimental training data 160. For example, some implementations of the system can use the simulation data available from the Materials Project, which include data for more than 100,000 compounds, and use the experimental training data available from the SGTE Solid SUBstance dataset, which includes fewer than 2,000 unique chemical compositions. However, the simulation data may not have adequate accuracy for predicting material properties. For example, DFT methods tend to produce large systematic errors due to the limitations of the underlying density functional approximations as well as other effects like the 0K approximation. Thus, the experimental training data 160 is useful for fine-tuning the model parameters 135 of the material property neural network.

In order to address the above challenges, the described techniques leverage the information in large simulation databases by learning a transferable embedding that enables accurate experimental property prediction even from small amounts of experimental data Examples of performing training of the material property prediction neural network 120 will be described below with reference to FIG. 4.

Briefly, the training engine 130 obtains the experimental training data 160 and the simulation training data 170, performs a first training of the graph neural network 122 and the simulation prediction neural network 129 using the simulation training data 170, and performs a second training of the graph neural network 122, the compositional neural network 124, and the experimental prediction neural network 128 using the experimental training data 160.

In some implementations, the training engine 130 can perform the first training and second training separately. That is, the experimental prediction neural network 128 is not trained as part of the first training, and the simulation prediction neural network 129 is not trained as part of the second training.

In some other implementations, the training engine 130 can perform the first training and second training jointly. For example, the training engine 130 can express a total loss L as a combination of the simulation loss and the experimental loss, and updates the model parameters 135 of the graph neural network 122, the simulation prediction neural network 129, the compositional neural network 124, and the experimental prediction neural network 128 based on the total loss.

In some implementations, in performing the joint training, the system can adjust respective weights assigned to the first training and the second training as the joint training progresses. This way, the system can rely more on the simulation training data in the early portion of the training process, and increasingly rely more on the experimental training data to fine-tune the network parameters as the training progresses.

Figure 2:
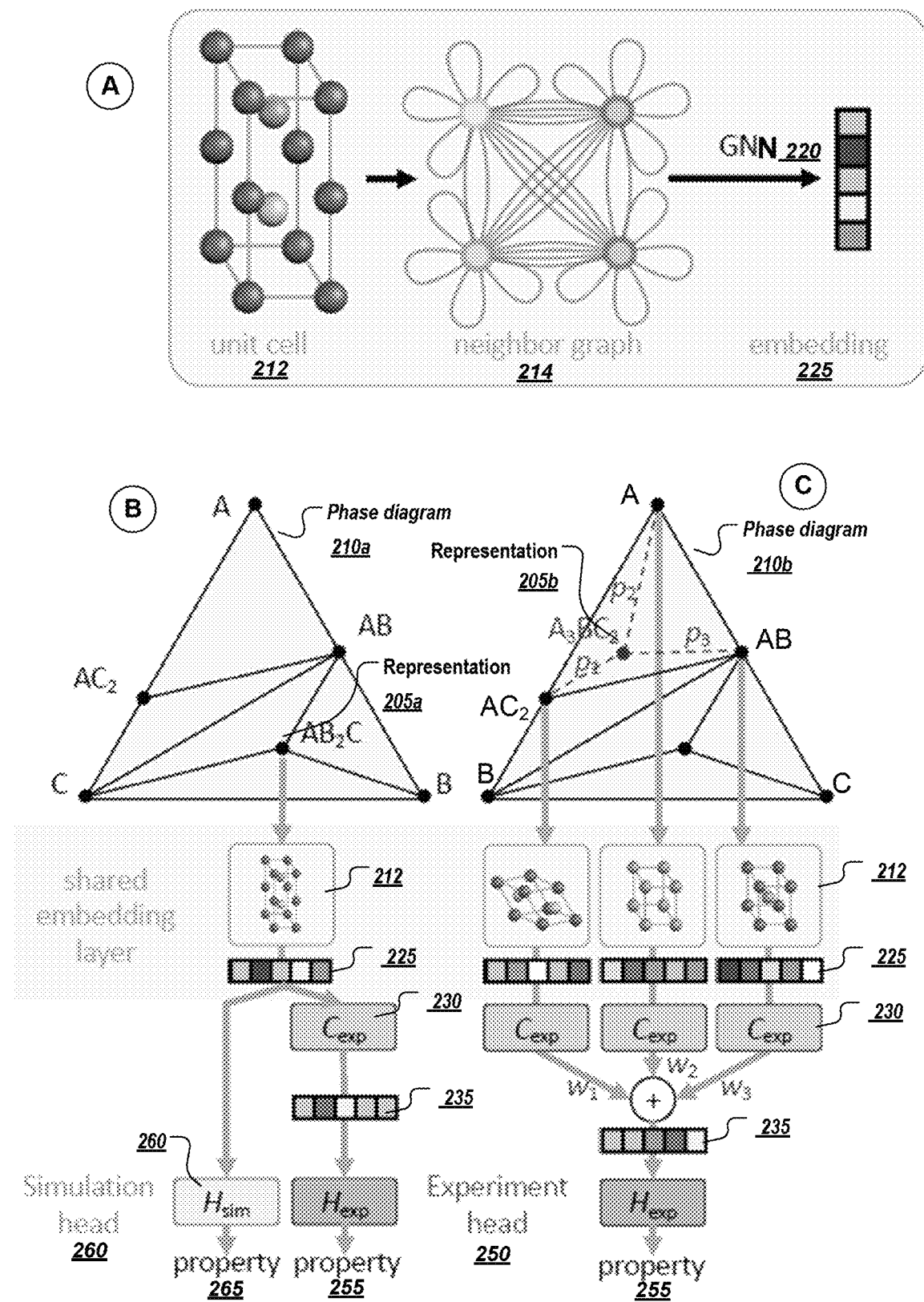
FIG. 2 illustrates examples of predicting a property of a material and training a material property prediction neural network using experimental data and simulation data.

FIG. 2 illustrates examples of generating a graph representation and embedding of a physical structure of a material, predicting the simulated and experimental properties of the material using a material property prediction neural network, and training the material property prediction neural network using experimental data and simulation data. For convenience, those processes will be described as being performed by a system of one or more computers located in one or more locations. For example, a material property prediction system, e.g., the material property prediction system 100 of FIG. 1, appropriately programmed in accordance with this specification, can perform the processes illustrated in FIG. 2.

As shown in portion (A) of FIG. 2, a material physical structure 212 can be an atomistic structure of a unit cell of the crystal of the corresponding material. The material property prediction system can generate the graph representation 214 of the material physical structure 212 by representing the atoms of the unit cell structure of the material with nodes and assigning the respective atomic numbers as node features. The system can further connect the nodes representing atoms with inter-atom distances under a certain threshold with edges, and assign the respective inter-atom distances as edge features.

The system generates the embedding 225 of the material by processing the graph representation 214 with the graph neural network 220. The embedding 225 feature vector representation having a plurality of feature values. Since the embedding 225 is obtained by processing the graph representation 224 of the structure (e.g., atomistic structure 212) of the material, the embedding 225 is a feature vector that represents the structural feature of material.

As shown in portions (B) and (C) of FIG. 2, the material property prediction neural network has an architecture that includes the graph neural network "trunk" 220 that computes the embedding of the material structure, and two "heads", including an experiment head 250 that regresses an input embedding to experimental values and a simulation head 260 that regresses an input embedding to simulation values to material properties. The material property prediction neural network further includes a compositional neural network 230 that process the embedding 225 to generate an experimental embedding 235.

A goal of the training is to transfer knowledge from material simulation data to the experiment head 250 by the shared graph neural network trunk 220. The system can perform training of the graph neural network trunk 220 and the simulation head 260 on simulation data to learn structure□property relations, and use the experimental data to fine-tune the graph neural network trunk 220 and the experimental head 255.

As shown by portion (B) of FIG. 2, for materials (e.g., chemical compounds) specified in the simulation dataset, the system uses the simulation head 260 to compute a prediction for the simulated properties 265 from the embedding 225. For a new material (e.g., a chemical compound) or a material specified in the experimental dataset that has a stable correspondence in the simulation dataset, e.g., the compound represented by $AB_2C$ (205a), the system can use the compositional neural network 230 to process the embedding generated for the structure of the corresponding material in the simulation dataset, and generate the experimental embedding 235. The system further uses the experiment head 250 to process the experimental embedding 235 to compute a prediction for the experimental properties 255.

As shown by portion (C) of FIG. 2, for a new material or an experimental material that does not have a stable correspondence in the simulation dataset, the system can generate a representation 205b of the material using a phase diagram 210b. For example, the representation 205b can be a weighted combination of a plurality of similar materials (shown by the black dots in the phase diagram 210b) specified in the simulation dataset.

For each of the plurality of similar materials, the system generates the graph representation 212 of the similar material, processes the graph representation 212 using the graph neural network 220 to generate the embedding 225, and processes the embedding 225 with the compositional neural network 230 to generate an experimental embedding of the similar material. The system further generates the experimental embedding 235 of the new material or the experimental material by performing an interpolation using the weight coefficients in weighted combination representation. An example process of generating the experimental embedding 235 will be described in more details in reference to FIG. 3B. After the experimental embedding 235 of the new material or the experimental material has been generated, the system uses the experiment head 250 to process the experimental embedding 235 to compute a prediction for the experimental properties 255.

Figure 3A:
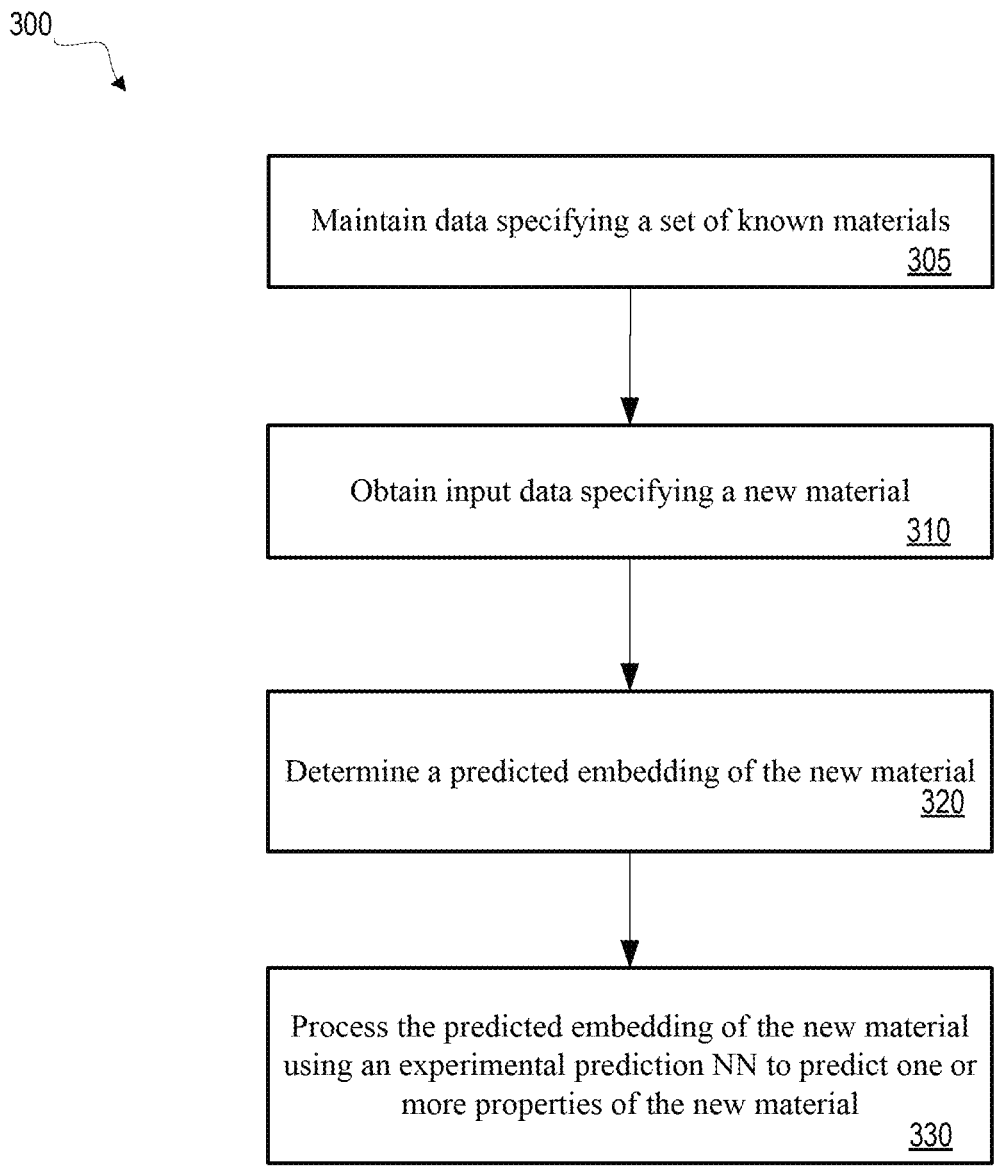
FIG. 3A is a flow diagram illustrating an example process for predicting material properties of a material using neural networks.

FIG. 3A is a flow diagram illustrating an example process 300 for predicting material properties of a material using neural networks. For convenience, the process 300 will be described as being performed by a system of one or more computers located in one or more locations. For example, a material property prediction system, e.g., the material property prediction system 100 of FIG. 1, appropriately programmed in accordance with this specification, can perform the process 300.

In general, the process 300 aims to predict experimental properties of a material using a neural network by leveraging available data of one or more similar materials in a dataset of known materials. A feature of the process 300 is that the material property prediction system generates material descriptors, i.e., embeddings, from the dataset of known materials using a graph neural network based on the structures, such as atomistic structures, of the known materials. Since the unit cell structure of a material underpins its quantum mechanical properties, the structured models used by the material property prediction system instill physically plausible inductive biases in the neural network, and thus can achieve high accuracy of the prediction and allow the network to be trained more effectively with smaller amounts of data.

In Step 305, the system maintains a data set specifying a set of known materials. For each known material in the set, the data set specifies a respective physical structure of the known material. The physical structure of a known material can be an atomistic structure, for example, an atomistic structure of a unit cell of the crystal of the known material. In some implementations, the physical structures of one or more of the known materials in the set are determined through simulations that model the atomistic structures of the material, such as using the DFT simulations.

In Step 310, the system obtains data specifying a new material. The data specifying the new material can include a chemical composition (e.g., a chemical formula) of the new material. The physical structure and material properties of the new material may be unknown.

In Step 320, the system determines a predicted embedding of the new material. An implementation example of determining the predicted embedding of the new material will be described below with reference to FIG. 3B. Briefly, in this step, the system identifies one or more known materials in the data set that are similar to the new material, and determines the predicted embedding of the new material based on at least the respective embeddings of the similar known materials. The embedding of a similar known material represents the physical structure (e.g., the atomistic structure) of the known material, and is generated by processing a graph representation of the physical structure of the similar known material using a graph neural network.

In Step 330, the system processes the predicted embedding of the new material using an experimental prediction neural network to predict one or more properties of the new material. An example of the predicted properties of the new material is the formation energy of the new material. Other examples of the predicted properties of the new material include the energy of decomposition, the band gap, and resistivity of the new material.

In some implementations, for each of the one or more properties, the experimental prediction neural network is a feedforward neural network configured to regress the predicted embedding of the new material to a predicted value of the one or more properties. An example of the experimental prediction neural network is a multi-layer perceptron (MLP) network.

Figure 3B:
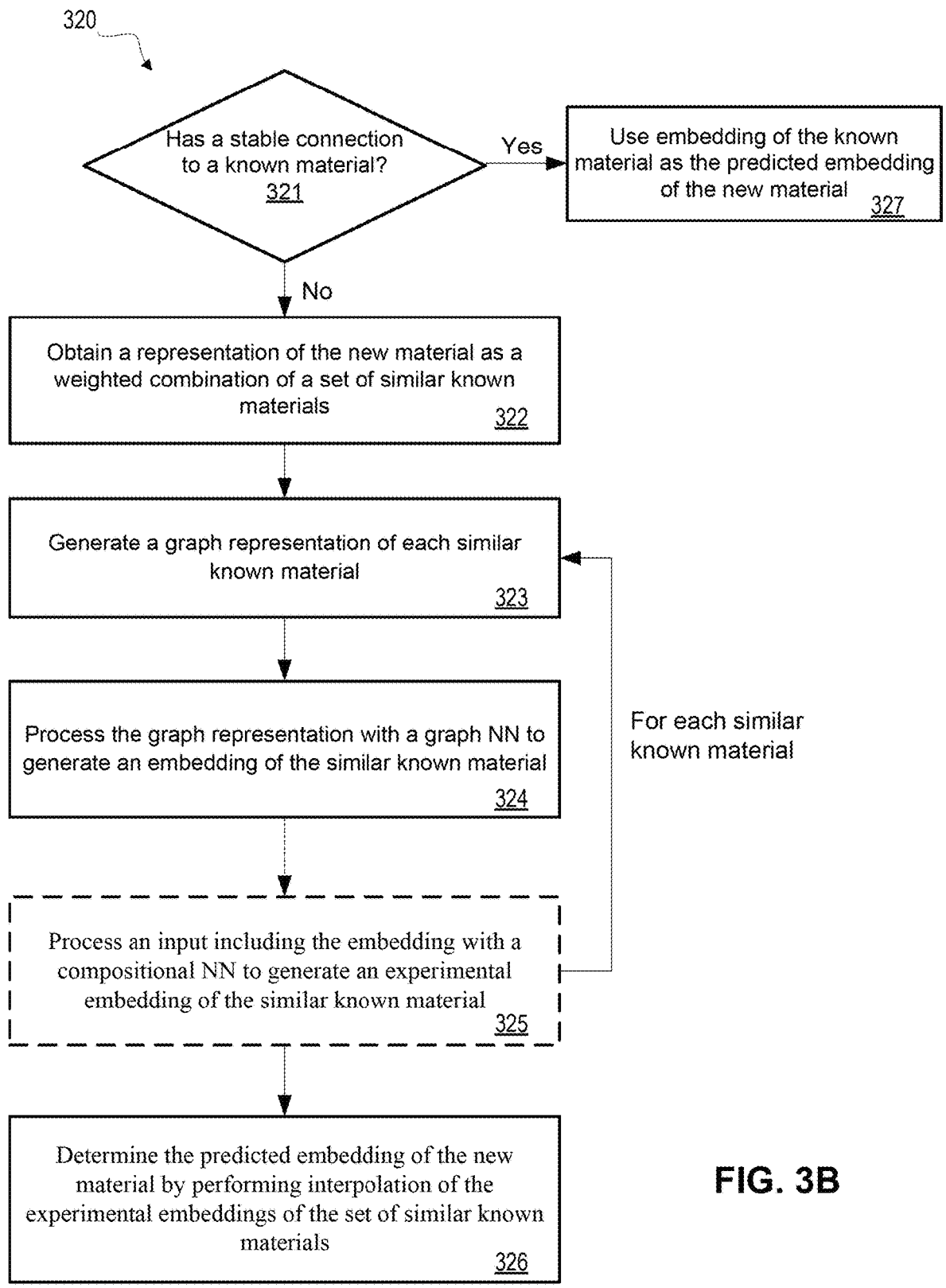
FIG. 3B is a flow diagram illustrating an example process for determining an embedding of the material.

FIG. 3B is a flow diagram illustrating an example process 320 for determining the embedding of the material. For convenience, the process 320 will also be described as being performed by a system of one or more computers located in one or more locations, such as the material property prediction system 100 of FIG. 1.

In step 321, the system determines whether the new material has a stable correspondence to any of the known materials in the set. For example, in some implementations, if the system identifies a known material y in the set of know materials that has a chemical composition (e.g., a chemical formula) that matches the chemical composition of the new material x, the system can assume that the new material x has a stable correspondence to the know material y.

If the system determines that the new material does not have a stable correspondence to any of the known materials in the set, the system proceeds to perform steps 322-326 to generate predicted embedding of the new material.

In step 322, the system generates a representation of the new material x as a weighted combination of the plurality of similar known materials $y_1, \ldots, y_n \in Y$.

In some implementations, the system uses compositional phase diagrams to identify the plurality of similar known materials $y_1, \ldots, y_n$ for the new material x and to obtain the representation of the new material x as a weighted combination of the plurality of similar known materials with the respective weights $p_1, \ldots, p_n$.

Phase diagrams can be used to represent the thermodynamic phase equilibria of multicomponent systems. An example of a ternary compositional phase diagram 210a is shown in portion (B) of FIG. 2. The compositional phase diagram 210a represents a compositional space of multicomponent systems composed of elements A, B, and C. The black nodes on the compositional phase diagram 210a represent phases of known materials that have been determined to be stable under given conditions. The solid lines in the phase diagram 210a are projections of the convex hull construction into the compositional space. These lines form the Gibbs triangles, which can be used to find stable phases of compositions of elements A, B, and C.

Portion (C) of FIG. 2 shows an example of using the compositional phase diagram 210b to determine the representation for a new material, e.g., $A_3BC_2$. As shown in portion (C) of FIG. 2, for the new material x (i.e. $A_3BC_2$), the system can identify the neighboring nodes A, AB, and $AC_2$ of the node representing the new material, and identify the stable known materials represented by the neighboring nodes as the similar known materials $y_1, \ldots, y_3$ of the new material x. The dashed line sections shown in portion (C) of FIG. 2 are projections of the convex hull construction of the new material into the compositional space represented by the compositional phase diagram, and represent the respective weights $p_1, \ldots, p_3$ in the weighted combination representation for the new material.

In general, according to the compositional phase diagrams, the system can obtain the representation of the new material x as the weighted combination of the plurality of similar known materials. The system can obtain the compositional phase diagrams according to the physical structures and/or properties (e.g., formation energies) of the known materials. The phase diagrams can be constructed using any suitable computation methods or suitable computational software packages, such as the Pymatgen software.

After the system identifies the plurality of similar known materials $y_1, \ldots, y_n \in Y$ and weights $p_1, \ldots, p_n$ for the new material x in step 322, the system performs steps 323-325 for each similar known material $y_i$ in the plurality of similar known materials $y_1, \ldots, y_n$ to obtain an experimental embedding for the similar known material $y_i$.

In step 323, the system generates a graph representation $g(y_i)$ of the similar known material $y_i$. The system can construct the graph representation $g(y_i)$ based on the physical structure (e.g. atomistic structure) of the similar known material $y_i$. For example, the system can construct the graph representation $g(y_i)$ by representing the atoms of the unit cell structure of the material $y_i$ with nodes and assigning the respective atomic numbers as node features. The system can further connect the nodes representing atoms with inter-atom distances under a certain threshold with edges, and assign the respective inter-atom distances as edge features. 324

In step 324, the system processes the graph representation $g(y_i)$ with a graph neural network T to generate an embedding $v_T(y_i)=T(g(y_i))$ of the similar known material $y_i$. Since the embedding $v_T(y_i)$ is obtained by processing the graph representation $g(y_i)$ of the structure (e.g., atomistic structure) of the material $y_i$, the embedding $v_T(y_i)$ is a embedding of structural feature of material $y_i$. An example of graph representation 214 and embedding 225 of a material physical structure 212 is illustrated in portion (A) of FIG. 2.

In some implementations, the physical structure and other properties of a similar known material $y_i$ are determined through simulations that model the atomistic structures of the material, such as using the DFT computations. For such a similar known material, the embedding $v_T(y_i)$ is an embedding based on simulated material features. The system can perform another step 325, to process an input that includes the embedding with a compositional neural network $C_{exp}$ to generate an experimental embedding $v_{exp}(y_i)=C_{exp}(v_T(y_i))$ of the similar known material $y_i$.

In some implementations, the input to the compositional neural network $C_{exp}$ further includes one or more values (e.g., simulated values) for one or more respective properties of the similar known material $y_i$. For example, the system can generate the input to the compositional neural network by combining, e.g., concatenating, a simulated formation energy value with the embedding $v_T(y_i)$. Thus, the experimental embedding for the similar known material $y_i$ can be expressed as $v_{exp}(y_i)=C_{exp}([v_T(y_i),e_{sim}(y_i)])$, where [,] denotes the concatenation operation. The combined input provides additional information to the compositional neural network, allowing the compositional neural network to learn corrections over the simulation predictions depending on the structure of the material.

In some other implementations, the system does not use a compositional neural network to process the embedding of the similar known material, and instead uses the embedding generated by the graph neural network as the experimental embedding of the similar known material.

Once the respective experimental embeddings $v_{exp}(y_i)$ for the plurality of similar known materials are obtained, in step 326, the system determines the predicted embedding $\bar{v}_T(x)$ of the new material x by performing interpolation of the experimental embeddings of the similar known materials. For example, the system can perform the interpolation based on the representation of the weighted combination of the plurality of similar known materials, and compute the predicted embedding $\bar{v}_T(x)$ of the new material x as a weighted combination of the experimental embeddings $v_{exp}(y_i)$ for the plurality of similar known materials. In one example, the system compute the predicted embedding $\bar{v}_T(x)$ of the new material x as $$\bar{v}_T(x) = \sum_{i=1}^{n} w_i v_{exp}(y_i), \quad w_i = \frac{p_i^\alpha}{\sum_{i=1}^{n} p_i^\alpha}, \tag{1}$$

where $\alpha$ is a parameter controlling how component embeddings are interpolated, and the weigh coefficients $w_i$ are normalized coefficients based on the respective weights $p_i, \ldots, p_n$ in the weighted combination representation for the new material x.

In equation (1), setting the parameter $\alpha$ to 0 averages all stable neighbors uniformly. Setting $\alpha$ to $\infty$ uses the stable neighbour with the largest weight only. In some implementations, the system uses $\alpha=1$ in equation (1) to calculate the predicted embedding $\bar{v}_T(x)$ of the new material. In this case, the weigh coefficients $w_i$ are normalized weights $p_1, \ldots, p_n$ in the weighted combination representation for the new material x obtained from the phase diagram decomposition.

Referring back to step 321, if the system determines that the new material x does have a stable correspondence to a known material y, the system performs step 327 to generate the embedding of the known material based on the embedding of the known material y. The system can determine the embedding of the known material y using a process similar to that described in steps 323-325. For example, the system can generate the graph representation g(y) of the known material y, process the graph representation g(y) using the graph neural network to generate the embedding $v_T(y)$ of the known material y, optionally process an input including the embedding $v_T(y)$ using the compositional neural network to generate the experimental embedding $v_{exp}(y)$ for the known material y, and uses the $v_{exp}(y)$ of the known material y as the embedding of the known material x. That is, the system compute the predicted embedding $\bar{v}_T(x)$ of the new material x as $\bar{v}_T(x)=v_{exp}(y)$. Note that this expression can be obtained from equation (1) by assigning n=1. Thus, equation (1) can be considered to describe a unified method to compute the embedding of the new material based on one or more similar known materials.

Figure 4:
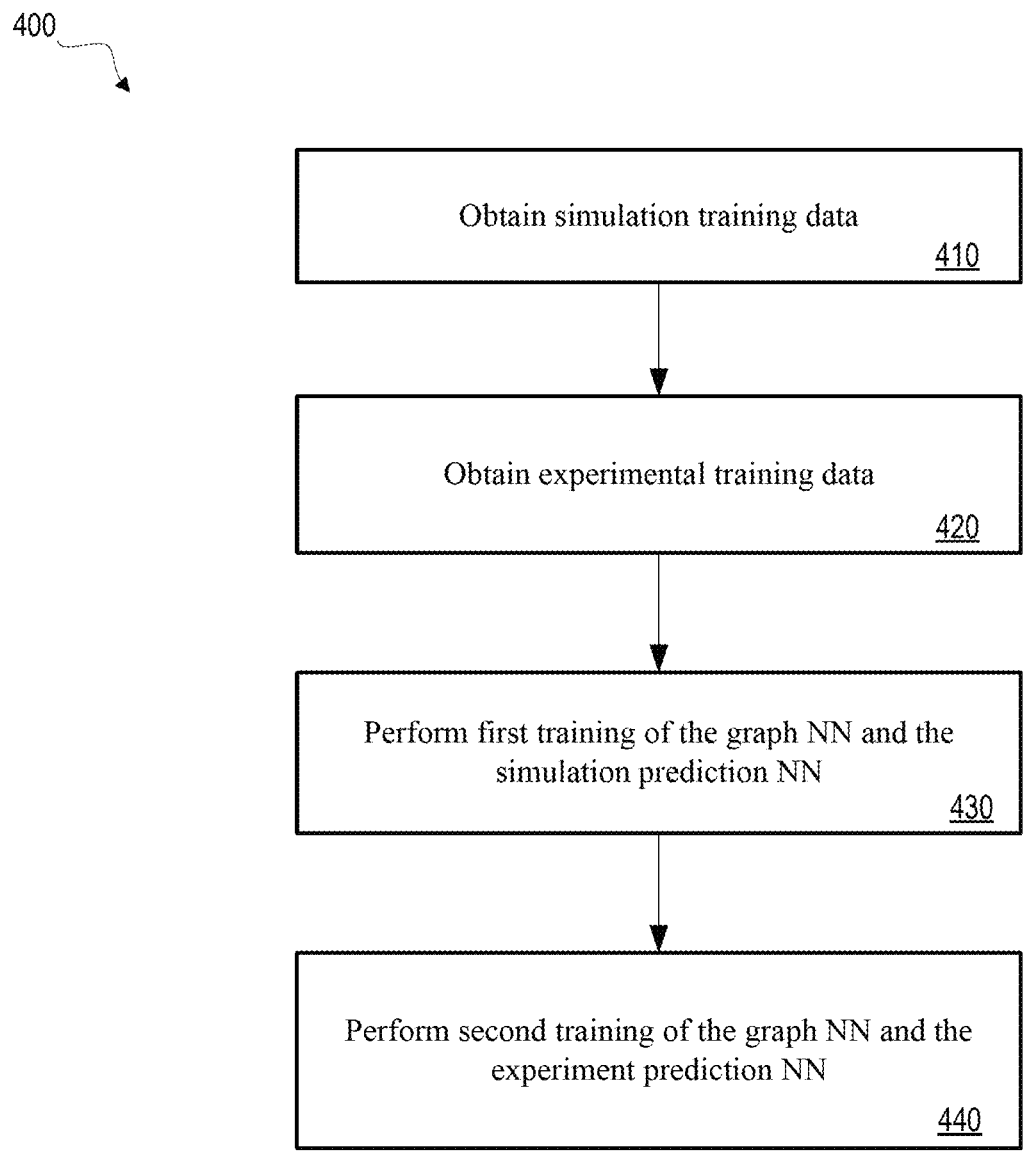
FIG. 4 is a flow diagram illustrating an example process for training a material property prediction neural network.

FIG. 4 is a flow diagram illustrating an example process 400 for training a material property prediction neural network. For convenience, the process 400 will be described as being performed by a system of one or more computers located in one or more locations. For example, a material property prediction system, e.g., the material property prediction system 100 of FIG. 1, appropriately programmed in accordance with this specification, can perform the process 400.

In some implementations, the material property prediction neural network has an architecture that includes a graph neural network "trunk" that computes an embedding of a material structure, and two "heads": one to regress experimental values and another for simulation values to material properties. A goal of the training is to transfer knowledge from material simulation data to the experiment "head" by the shared graph neural network "trunk". The system can perform training of the graph neural network "trunk" and the simulation "head" on simulation data to learn structure☐property relations, and use the experimental data to fine-tune the graph neural network "trunk" and the experimental "head".

An example structure of the material property prediction neural network is shown as 120 in FIG. 1. The material property prediction neural network includes: a graph neural network (e.g., 122 in FIG. 1), a compositional neural network (e.g., 124 in FIG. 1), an experimental prediction neural network (e.g., 128 in FIG. 1), and a simulation prediction neural network (e.g., 129 in FIG. 1).

The graph neural network is configured to process a graph representation of a physical structure of a material and to generate an embedding of the material. The graph representation can be based on an atomistic structure of the material. For example, the graph representation can represent atoms of the unit cell structure of the material with nodes having the respective atomic numbers as node features. The graph representation can further include edges that connect the nodes representing atoms with inter-atom distances under a certain threshold. The edges can have the respective inter-atom distances as edge features.

The compositional neural network is configured to process the embedding of the material to generate an experimental embedding. The experimental prediction neural network is configured to process the experimental embedding to predict properties of the material that would be measured in a physical experiment. The simulation prediction neural network is configured to process the embedding of the material and predict properties of the material that would be measured in a simulation.

Each of the graph neural network, the compositional neural network, the experimental prediction neural network, and the simulation prediction neural network, can be implemented with any suitable network architecture, and can include one or more fully-connected layers, convolution layers, rectified linear unit layers, batch normalization layers, or pooling layers. The graph neural network can further include one or more message passing layers that operate on the feature representations of the nodes and edges of the graph representation of the material structure.

In step 410, the system obtains simulation training data. The simulation training data includes a plurality of simulation training examples that respectively specify a plurality of materials for which simulations have been performed to predict one or more material properties. For convenience, a material specified by a simulation training example in the simulation data is termed a "first material". For each of the plurality of first materials, the corresponding simulation training example includes a physical structure of the first material and simulated values for each of the one or more properties that were measured in a simulation of the first material.

In some implementations, the physical structure specified by each simulation training example is an atomistic structure, for example, an atomistic structure of a unit cell of the crystal of the corresponding first material. The physical structure of the first material can be determined through simulations that model the atomistic structures of the material, such as using the DFT computations.

The material properties specified in each simulation training example can include the formation energy of the material. Other examples of the material properties of the first material include the energy of decomposition, the band gap, and the resistivity of the material. These material properties can also be determined through simulations that model the atomistic structures of the material (e.g., DFT simulations), and the simulated values of one or more of the material properties are included in the simulation training examples.

Since simulation data is relatively inexpensive to obtain, the simulation training data can include a relatively large number (e.g., >10,000) of simulation training examples. For example, some implementations of the system can use the simulation data available from the Materials Project, which include data for more than 100,000 compounds.

In step 420, the system obtains experimental training data. The experimental training data includes experimental training examples that respectively specify a plurality of materials for which experimental measurements have been performed to obtain one or more material properties. For convenience, a material specified by an experimental training example is termed a "second material". For each of the plurality of second materials, the corresponding experimental training example includes experimentally measured values for each of the one or more properties. For example, each experimental training example can include one or more experimentally measured values for the formation energy, the energy of decomposition, the band gap, and/or the resistivity of the corresponding second material.

In some implementations, for each second material, the corresponding experimental training example includes a chemical composition (e.g., a chemical formula) of the second material to specify the second material. In some implementations, experimental data is available for physical structures (e.g., the atomistic structures) of one or more second materials, and the physical structures are included in the corresponding experimental training examples to specify the corresponding second materials. In some other implementations, the physical structures of one or more of the second materials may not be readily available, and are not included in the corresponding training examples to specify the second materials. In those implementations, the second materials can be specified by their respective chemical compositions (e.g., a chemical formulas) in the experimental training examples.

Since experimental data is typically more costly to obtain compared to simulation data, the experimental training data can include a relatively small number (e.g., <10,000) of experimental training examples. For example, some implementations of the system can obtain the experimental training data from the SGTE Solid SUBstance dataset, which includes fewer than 2,000 unique chemical compositions.

In step 430, the system performs training of the graph neural network and the simulation prediction neural network using the simulation training data. For convenience, the training using the simulation training data is termed the "first training".

In step 440, the system performs training of the graph neural network and the experimental prediction neural network using the experimental training data. For convenience, the training using the experimental training data is termed the "second training".

In some implementations, one or more of the experimental training examples specify the second materials using chemical compositions (e.g., a chemical formulas), and do not include the physical structures of the respective second materials. In order to predict the material properties for a second material using the graph neural network and the experimental prediction neural network, the system can generate an embedding of the second material using an interpolation process. A similar process was described with reference to FIG. 3B.

Briefly, the system can determine whether the second material has a stable correspondence to any known material with known physical structure. If the system determines that the second material does have a stable correspondence to a known material with known physical structure, the system can process a graph representation of the known material with the graph neural network to generate an embedding for the second material, and proceed to predict the material properties based on the embedding.

If the system determines that the second material does not have a stable correspondence to a known material with known structure, the system generates a representation of the second material as a weighted combination of a plurality of similar known materials with known physical structures using a compositional phase diagram. For each of the similar known materials, the system generates a graph representation of the physical structure of the material, and processes the graph representation with the graph neural network to generate an embedding for the similar known material.

In some implementations, the physical structures and other properties of the plurality of materials are determined through simulations, and the system can process an input that includes the embedding of the material with the compositional neural network to generate an experimental embedding of the similar known material. In some implementations, the input to the compositional neural network further includes one or more values (e.g., simulated values) for one or more respective properties of the similar known material.

In some other implementations, the system does not use a compositional neural network to process the embedding of the similar known material, and instead uses the embedding generated by the graph neural network as the experimental embedding of the similar known material.

Once the respective experimental embeddings for the plurality of similar known materials are obtained, the system determines the predicted embedding of the second material by performing interpolation of the experimental embeddings of the similar known materials.

In some implementations, the first training is dedicated to the graph neural network and the simulation prediction neural network and does not involve training the experimental prediction neural network. In other words, the simulation training data is not used to update parameters of the experimental prediction neural network. During the first training, the system can train the graph neural network and the simulation prediction neural network end-to-end based on a simulation loss $\varepsilon_{x \in S}[|\hat{e}_{sim}(x) - e_{sim}(x)|]$ measuring the difference between the material properties specified in the simulation training data $e_{sim}(x)$ and the predicted properties $\hat{e}_{sim}(x)$ outputted by the simulation prediction neural network. The system can update the network parameters of the graph neural network and the simulation prediction based on $\varepsilon_{x \in S}$ through any appropriate backpropagation-based machine learning technique, e.g., using the Adam or AdaGrad optimizers.

Similarly, in some implementations, the second training is dedicated to the graph neural network, the compositional neural network, and the experimental prediction neural network, and does not involve training the simulation prediction neural network. In other words, the experimental training data is not used to update parameters of the simulation prediction neural network. During the second training, the system can train the graph neural network, the compositional neural network, and the experimental prediction neural network end-to-end based on an experimental loss $\varepsilon_{x \in E}[|\hat{e}_{exp}(x) - e_{exp}(x)|]$ measuring the difference between the material properties specified in the experimental training data $e_{exp}(x)$ and the predicted properties $\hat{e}_{exp}(x)$ outputted by the experimental prediction neural network. The system can update the network parameters of the graph neural network, the compositional neural network, and the experimental prediction based on $\varepsilon_{x \in E}$ through any appropriate backpropagation-based machine learning technique, e.g., using the Adam or AdaGrad optimizers.

In some implementations, the system can perform the first and the second trainings jointly by expressing a total loss $\mathcal{L}$ as a combination of the simulation loss $\varepsilon_{x \in S}$ and the experimental loss $\varepsilon_{x \in E}$, and updating the network parameters of the graph neural network, the simulation prediction neural network, the compositional neural network, and the experimental prediction neural network based on the total loss.

In some implementations, in performing the joint training, the system can adjust respective weights assigned to the first training and the second training as the joint training progresses. The total loss of this process can be represented by $$\mathcal{L}(t) = \omega_{sim}(t)\varepsilon_{x \in S} + \omega_{exp}(t)\varepsilon_{x \in E} \qquad (2)$$

where t represents the training iteration, and the respective weights $\omega_{sim}(t)$ and $\omega_{exp}(t)$ for the simulation loss (for the first training) and the experimental loss (for the second training) are adjusted over the progression of the joint training.

In some implementations, the system can increase the weight $\omega_{exp}(t)$ assigned to the second training relative to the weight $\omega_{sim}(t)$ assigned to the first training as the joint training progresses. Thus, the system can rely more on the simulation training data in the early portion of the training process, and increasingly rely more on the experimental training data to fine-tune the network parameters as the training progresses.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by a data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, which is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., experimental predictionROM, Experimental prediction-ROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially be claimed as such, one or more features from a claimed combination can in some cases be excised from the combination, and the claimed combination may be directed to a sub-combination or variation of a sub-combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the

What is claim is:

1. A method performed by one or more computers, the method comprising:
maintaining data specifying a set of known materials each having a respective known physical structure;
receiving data specifying a new material;
identifying a plurality of similar known materials in the set of known materials that are similar to the new material;
determining a predicted embedding of the new material from at least respective embeddings corresponding to each of the plurality of similar known materials, each respective embedding representing the respective known physical structure of a corresponding similar known material in the plurality of similar known materials; and
processing the predicted embedding of the new material using an experimental prediction neural network to predict one or more properties of the new material;
wherein the experimental prediction neural network has been trained as a component of a material property prediction neural network comprising (i) a graph neural network configured to receive a graph representation of a physical structure of a material and to generate, from the graph representation, an embedding of the material, (ii) the experimental prediction neural network configured to receive an experimental embedding derived from the embedding of the material and predict one or more properties of new material that would be measured in a physical experiment on the material, and (iii) a simulation prediction neural network configured to receive the embedding of the material and predict one or more properties of the new material that would be measured in a simulation on the material, wherein the material property prediction neural network has been trained by:
performing first training of the graph neural network and the simulation prediction neural network on simulation training data that comprises, for each of a plurality of first materials (i) data identifying a physical structure of the first material and (ii) simulated values for each of the one or more properties that were measured in a simulation of the first material; and
performing second training of at least the graph neural network and the experimental prediction neural network on experimental training data that comprises, for each of a plurality of second materials, experimental values for each of the one or more properties that were measured in a physical experiment on the second material.

2. The method of claim 1, wherein, for each of the one or more properties, the experimental prediction neural network is configured to regress a predicted value of the one or more properties.

3. The method of claim 2, wherein the one or more properties include an energy of formation of the new material.

4. The method of claim 1, further comprising:
determining that the new material does not have a stable correspondence to any of the known materials in the set of known materials, wherein:
identifying the plurality of similar known materials, determining the predicted embedding, and processing the predicted embedding are performed in response to determining that the new material does not have a stable correspondence to any of the known materials in the set of known materials.

5. The method of claim 4, further comprising:
receiving data specifying a second new material;
determining that the second new material has a stable correspondence to a second known material in the set of known materials;
determining a predicted embedding of the second new material from an embedding of the second known material that represents the known physical structure of the second known material; and
processing an experimental embedding derived from the predicted embedding of the second new material using the experimental prediction neural network to predict one or more properties of the second new material.

6. The method of claim 1, wherein identifying a plurality of known materials in the set of known materials that are similar to the new material comprises:
identifying the plurality of similar known materials by generating a representation of the new material as a weighted combination of the plurality of similar known materials that assigns a respective weight to each of the plurality of similar known materials.

7. The method of claim 6, wherein identifying a plurality of known materials in the set of known materials that are similar to the new material comprises:
identifying the plurality of similar known materials and generating the representation through phase diagram decomposition.

8. The method of claim 6, wherein determining a predicted embedding of the new material from at least respective embeddings corresponding to each of the similar known materials comprises:
for each of the plurality of similar known materials, generating an experimental embedding of the similar known material from the embedding of the similar known material; and
generating the predicted embedding of the new material by performing an interpolation between the experimental embeddings using the weights assigned to the similar known materials in the weighted combination.

9. The method of claim 8, wherein generating the experimental embedding of the similar known material comprises:
processing an input comprising the embedding using a compositional neural network to generate the experimental embedding.

10. The method of claim 9, wherein the input further comprises, for each of one or more of the one or more properties, a simulated value of the property for the similar known material.

11. The method of claim 1, wherein the data specifying the new material is a chemical formula of the new material.

12. The method of claim 1, further comprising:
generating the respective embeddings of each of the plurality of similar known materials, comprising, for each of the similar known materials:
generating a graph representation of the known physical structure of the similar known material; and
processing the graph representation of the known physical structure using a graph neural network to generate the embedding of the similar known material.

13. The method of claim 1, wherein the known physical structure is an atomistic structure of the known material.

14. The method of claim 1, wherein the experimental prediction neural network is a feedforward neural network that is configured to process the predicted embedding to regress predicted values of the one or more properties of the new material.

15. The method of claim 1, wherein the first training and second training have been performed jointly.

16. The method of claim 15, wherein the first training and second training have been trained in a joint training that comprises adjusting respective weights assigned to the first training and the second training as the joint training progresses.

17. A system comprising:
one or more computers; and
one or more storage devices storing instructions that when executed by the one or more computers, cause the one or more computers to perform:
  maintaining data specifying a set of known materials each having a respective known physical structure;
  receiving data specifying a new material;
  identifying a plurality of similar known materials in the set of known materials that are similar to the new material;
  determining a predicted embedding of the new material from at least respective embeddings corresponding to each of the plurality of similar known materials, each respective embedding representing the respective known physical structure of a corresponding similar known material in the plurality of similar known materials; and
  processing the predicted embedding of the new material using an experimental prediction neural network to predict one or more properties of the new material;
  wherein the experimental prediction neural network has been trained as a component of a material property prediction neural network comprising (i) a graph neural network configured to receive a graph representation of a physical structure of a material and to generate, from the graph representation, an embedding of the material, (ii) the experimental prediction neural network configured to receive an experimental embedding derived from the embedding of the material and predict one or more properties of new material that would be measured in a physical experiment on the material, and (iii) a simulation prediction neural network configured to receive the embedding of the material and predict one or more properties of the new material that would be measured in a simulation on the material, wherein the material property prediction neural network has been trained by:
    performing first training of the graph neural network and the simulation prediction neural network on simulation training data that comprises, for each of a plurality of first materials (i) data identifying a physical structure of the first material and (ii) simulated values for each of the one or more properties that were measured in a simulation of the first material; and
    performing second training of at least the graph neural network and the experimental prediction neural network on experimental training data that comprises, for each of a plurality of second materials, experimental values for each of the one or more properties that were measured in a physical experiment on the second material.

18. One or more non-transitory computer-readable storage media storing instructions that, when executed by one or more computers, cause the one or more computers to perform:
  maintaining data specifying a set of known materials each having a respective known physical structure;
  receiving data specifying a new material;
  identifying a plurality of similar known materials in the set of known materials that are similar to the new material;
  determining a predicted embedding of the new material from at least respective embeddings corresponding to each of the plurality of similar known materials, each respective embedding representing the respective known physical structure of a corresponding similar known material in the plurality of similar known materials; and
  processing the predicted embedding of the new material using an experimental prediction neural network to predict one or more properties of the new material;
  wherein the experimental prediction neural network has been trained as a component of a material property prediction neural network comprising (i) a graph neural network configured to receive a graph representation of a physical structure of a material and to generate, from the graph representation, an embedding of the material, (ii) the experimental prediction neural network configured to receive an experimental embedding derived from the embedding of the material and predict one or more properties of new material that would be measured in a physical experiment on the material, and (iii) a simulation prediction neural network configured to receive the embedding of the material and predict one or more properties of the new material that would be measured in a simulation on the material, wherein the material property prediction neural network has been trained by:
    performing first training of the graph neural network and the simulation prediction neural network on simulation training data that comprises, for each of a plurality of first materials (i) data identifying a physical structure of the first material and (ii) simulated values for each of the one or more properties that were measured in a simulation of the first material; and
    performing second training of at least the graph neural network and the experimental prediction neural network on experimental training data that comprises, for each of a plurality of second materials, experimental values for each of the one or more properties that were measured in a physical experiment on the second material.

* * * * *